United States Patent
Rood

(10) Patent No.: US 6,977,081 B1
(45) Date of Patent: Dec. 20, 2005

(54) FACIAL CREAM COMPOSITION CONTAINING ALLANTOIN

(75) Inventor: Gloria Rood, Maple Grove, MN (US)

(73) Assignee: Upsher-Smith Laboratories, Inc., Minneapolis, MN (US)

( * ) Notice: Subject to any disclaimer, the term of this patent is extended or adjusted under 35 U.S.C. 154(b) by 0 days.

(21) Appl. No.: 10/323,099

(22) Filed: Dec. 18, 2002

(51) Int. Cl.[7] .......................... A61K 7/00; A61K 9/14; A61K 31/415
(52) U.S. Cl. ...................... 424/401; 424/400; 424/485; 424/725; 424/737; 424/744; 514/390; 514/783; 514/859; 514/937; 514/938
(58) Field of Search ................ 424/400, 401, 424/485, 725, 737, 744; 514/390, 783, 859, 514/937, 938

(56) References Cited

U.S. PATENT DOCUMENTS

| | | | |
|---|---|---|---|
| 4,388,301 A | 6/1983 | Klein | 424/154 |
| 5,445,823 A | 8/1995 | Hall et al. | 424/401 |
| 6,296,880 B1 | 10/2001 | Murad | 424/616 |
| 6,429,231 B1 | 8/2002 | Bhagwat et al. | 514/603 |
| 6,514,489 B1 | 2/2003 | Shacknai et al. | 424/70.1 |
| 2002/0082279 A1 * | 6/2002 | Schultz | 514/330 |
| 2002/0132015 A1 | 9/2002 | Shacknai et al. | 424/703 |
| 2002/0164381 A1 | 11/2002 | Shacknai et al. | 424/703 |
| 2003/0118526 A1 * | 6/2003 | Stiefel | 424/59 |
| 2004/0048836 A1 * | 3/2004 | Wilmott | 514/159 |

FOREIGN PATENT DOCUMENTS

JP  03-002124  1/1991

OTHER PUBLICATIONS

PDR entry for Sulfacet-R Lotion (Dermik), 1996.*

* cited by examiner

*Primary Examiner*—Gary Kunz
*Assistant Examiner*—Marina Lamm
(74) *Attorney, Agent, or Firm*—Faegre & Benson LLP

(57) ABSTRACT

The present invention provides emollient creams composed of sulfur, sodium sulfacetamide and a botanically-derived anti-inflammatory ingredient. The creams are alcohol-free and have a pH at or above 7.0.

9 Claims, No Drawings

FACIAL CREAM COMPOSITION CONTAINING ALLANTOIN

BACKGROUND OF THE INVENTION

Acne is a condition of the human skin characterized by an excess flow of sebum, or skin oil, from the sebaceous glands located in the pilosebaceious apparatus. Sebum reaches the skin surface through the duct of the hair follicle. The presence of excessive amounts of sebum in the duct and on the skin acts to block or stagnate the continuous flow of sebum from the follicular duct, thus producing a thickening and a solidification of the sebum to form a solid plug known as a comedone. When this process occurs, hyperkeratinization of the follicular opening is stimulated, thus completely closing the duct. The usual results are papules, pustules, or cysts, often contaminated with bacteria and/or bacterial growth, which cause secondary infections. Acne is particularly characterized by the presence of comedones, inflammatory papules, pustules or cysts. The effect of acne ranges from slight skin irritation to disfiguring scars.

It has been shown that skin products containing a combination of sulfur and sodium sulfacetamide are effective in treating acne, especially the secondary infections caused by bacteria. It is believed that sulfacetamides act as antagonists to para-aminobenzoic acid, an essential component for bacterial growth. Examples of acne treating substances incorporating these active ingredients include Sulfacet-R Lotion produced by Dermik Laboratories, Inc., Collegeville, Pa., and the sulfacetamide compositions reported in U.S. Pat. No. 6,429,231.

While the combination of sulfur and sodium sulfacetamide is an effective topical agent for the treatment of skin lesions consistent with acne, both of these active topical agents may tend to cause skin irritation in certain patients, effectively preventing these patients from benefiting from acne creams incorporating this combination. This skin irritation may be exacerbated when delivered by a base that contains substantial amounts of alcohol, for example, ethyl alcohol.

SUMMARY OF THE INVENTION

The present invention provides an emollient cream for treating acne. The emollient cream is composed of sulfur, sodium sulfacetamide and an anti-inflammatory compound. The emollient cream is alcohol-free and has a pH at or above about 7.0, more particularly between 7.5 and 7.6. The anti-inflammatory compound may include a botanically-derived compound, such as allantoin, witch hazel, aloe vera, chamomile, thyme extract, Echinacea or purslane extract. The emollient cream may include a base composed of an alcohol-free, oil-in-water emulsion.

DETAILED DESCRIPTION OF THE INVENTION

The emollient cream of the present invention may be composed of three phases: a gum phase, a water phase and an oil phase. The gum phase of the present invention includes sulfur, anhydrous sodium sulfacetamide and an anti-inflammatory compound. The sulfur may compose between about 1 w/w percent and 10 w/w percent of the cream and the sodium sulfacetamide may compose between about 5 w/w and 15 w/w percent of the cream. In one embodiment, the sulfur composes about 5 w/w percent of the cream and the sodium sulfacetamide composes about 10 w/w percent of the cream.

The anti-inflammatory compound may be a botanically-derived compound, such as allantoin, witch hazel, aloe vera, chamomile, thyme extract, Echinacea, purslane extract or combinations thereof. In one embodiment, the anti-inflammatory compound includes between about 0.1 and 1.0 w/w percent allantoin. The gum phase may also include between about 20.0 and 30.0 w/w percent purified water and between about 0.1 and 0.5 w/w percent of a suspending agent such as xanthan gum.

Allantoin, or (2,5-dioxo-4-imidazolidinyl)urea, is a white, odorless substance derived from the oxidation of uric acid. Allantoin is naturally present in many mammals and botanical sources, for example, tobacco seeds, sugar beets and wheat sprouts. Allantoin is a non-toxic, non-allergenic substance known for its anti-inflammatory, skin-softening (keratolytic effect) and rapid skin cell regeneration properties. It has previously been used as an abrasive and astringent agent in products such as cosmetic lotions, creams, suntan products, scalp preparations, shampoos, lipsticks and various aerosol preparations. It has also been used in topical pharmaceutical preparations, as well as various oral hygiene preparations such as toothpaste and mouthwash.

The water phase of the emollient cream may include glycols, preservatives and/or solvents. For example, the composition may include between about 20.0 and 30.0 w/w percent purified water, between about 2.0 and 6.0 w/w percent of a solvent such as propylene glycol, between about 0.2 and 1.0 w/w percent disodium ethylenediamine tetraacetic acid, between about 0.1 and 0.5 w/w percent sodium thiosulfate and between about 0.1 and 0.3 w/w percent methyl paraben.

The oil phase of the emollient cream may include fatty acids, waxes, glycols, and/or surfactants. In one embodiment of the present invention, the oil phase includes between about 2.0 and 6.0 w/w percent stearic acid, between about 5.0 and 10.0 w/w percent of PEG-8 stearate, between about 5.0 and 10.0 w/w percent emulsifying wax, between about 2.0 and 6.0 w/w percent isopropyl myristate, between about 2.0 and 6.0 w/w percent propylene glycol stearate and between about 0.1 and 0.3 w/w percent propyl paraben.

The emollient cream may also include between about 0.1 and 0.5 w/w percent of fragrance, as well as an effective amount of sodium hydroxide to maintain the pH of the cream at or above 7.0. In one embodiment, between about 1.0 and 5.0 w/w percent of a 10 w/w percent solution of sodium hydroxide may be added to the cream to maintain a pH at or above 7.0. In another embodiment, the pH of the solution may be maintained between about 7.5 and 7.6.

By maintaining the pH of the cream at or above 7.0, it has been found that the present invention exhibits a lower level of API-related degradents over time. For example, comparative emollient creams in which no pH adjustment was performed exhibited about 9.0 w/w percent degradents after 3 months of storage at 40° C. and 75% relative humidity. However, emollient creams produced according to the present invention having a pH at or above 7.0 had only about 2.0 w/w percent API-related degradents after 3 months of storage under the same conditions. This lower level of degradents may provide a cream with better efficacy and a longer shelf-life.

The emollient cream of the present invention has several beneficial characteristics for treating acne. First, the cream contains a botanically-derived anti-inflammatory compound, such as allantoin, which may reduce irritation associated with the application of sulfur and sodium sulfacetamide to the skin. Thus, a user of the cream may benefit from reduced appearance of acne, without experiencing significant inflammation.

Furthermore, the emollient cream of the present invention is alcohol-free. As used herein, the terms "alcohol free" and "free of alcohol" refer to the absence of monohydric alcohol compounds in the emollient cream of the present invention. It is well known that skin products containing alcohol tend to undesirably dry the skin, however, many anti-acne products include alcohol. Although the present invention contains glycol solvents, it does not contain drying agents, such as ethyl, stearyl and cetyl alcohol, which are often incorporated into conventional skin products. The alcohol-free cream of the present invention, combined with the anti-inflammatory botanical, may reduce both drying and inflammation of the skin, resulting in an anti-acne cream that causes less drying and inflammation, while still effectively treating acne.

The present invention may be further described by the embodiment set forth in the Example below.

EXAMPLE ONE EMBODIMENT

Gum (API) Phase Preparation

Xanthan Gum (3.2 kg) was hydrated and dispersed at ambient temperature in Purified Water, USP (417.5 kg) to produce a Gum (API) Phase. Sulfacetamide Sodium monohydrate (171.2 kg) was dispersed and dissolved into the Gum (API) Phase. Next, sulfur (80.0 kg) was suspended in the Gum (API) Phase. Finally, allantoin (8.0 kg) was dispersed in the Gum (API) Phase. The resulting mixture was then held aside until being added to the cooling emulsion formed from the Oil in Water Phase preparation described below.

Oil Phase Preparation

Isopropyl myristate (64.0 kg), propylene glycol stearate (64.0 kg), stearic acid (56.0 kg), emulsifying wax (112.0 kg), propyl paraben (3.2 kg) and PEG-8 stearate (120.0 kg) were heated in a primary compounding mix kettle with continuous stirring to 73–75° C. The resulting mixture was then maintained at this temperature prior to being combined with the Water phase.

Water Phase Preparation

Purified Water, USP (385.5 kg), was weighed into a jacketed side kettle. As the water was heated, propylene glycol (64.0 kg), methyl paraben (1.6 kg), disodium EDTA (8.0 kg), and sodium thiosulfate (4.8 kg) were added while mixing. When a temperature of 73–75° C. was reached, the phase was maintained at this temperature until the Oil Phase was added.

Oil in Water Emulsion Formation

The Water Phase was added to the Oil Phase by pumping the contents of the Water Phase into the Oil Phase. The contents of the Water Phase were transferred by pump to an inlet on the bottom of the primary compounding kettle. The resulting emulsion was mixed for fifteen minutes. Force cooling was initiated by reducing the jacket temperature to 53–55° C.

Gum (API) Phase Addition

When the Oil in Water emulsion temperature reached 53–55° C., the Gum Phase was added to the primary compounding kettle by pumping the contents of the Gum phase into an inlet at the bottom of the primary compounding kettle. The resulting Oil, Water and Gum ("three-phase") emulsion was mixed for fifteen minutes at between 53 and 55° C.

Final Cooling

Force cooling with stirring continued and the jacket temperature was reduced to 26–30° C. When the three-phase emulsion temperature reached 42–43° C., the fragrance (4.8 kg) was added. Force cooling continued until the temperature reached 26–30° C.

pH Adjustment

When the three-phase emulsion reached approximately ambient temperature, (26–30° C.), the pH of the final product was checked. The pH was adjusted to at or above 7.0, with a target range of 7.5 to 7.6, using a 10% solution of sodium hydroxide in water. This solution was made by combining sodium hydroxide pellets (6.4 kg) and water (57.6 kg). Approximately 40 kg of this solution was required to achieve the desired pH (about 2% of the total batch size).

The amount of each of the ingredients used in the above manufacturing process may be altered and varied to produce a skin cream within the ranges shown in Table 1.

TABLE 1

| COMPONENT | One Embodiment W/W% | RANGE |
| --- | --- | --- |
| Purified Water, USP | 50.2 | |
| Xanthan Gum, NF | 0.2 | 0.1–0.5 |
| Sulfacetamide Sodium, USP | 10.7 | 5.0–15.0 |
| Sulfur, Precipitated, USP | 5.0 | 1.0–10.0 |
| Allantoin | 0.5 | 0.1–1.0 |
| Isopropyl myristate, NF | 4.0 | 2.0–6.0 |
| Propylene glycol stearate | 4.0 | 2.0–6.0 |
| Stearic Acid, NF | 3.5 | 2.0–6.0 |
| PEG-8 Stearate | 7.5 | 5.0–10.0 |
| Emulsifying Wax, NF | 7.0 | 5.0–10.0 |
| Propyl paraben, NF | 0.2 | 0.1–0.3 |
| Propylene Glycol, USP | 4.0 | 2.0–6.0 |
| Methyl paraben, NF | 0.1 | 0.05–0.2 |
| Disodium EDTA, USP | 0.5 | 0.2–1.0 |
| Sodium Thiosulfate, USP | 0.3 | 0.1–0.5 |
| Fragrance | 0.3 | 0.1–0.5 |
| 10% sodium hydroxide Solution | q.s. to pH 7.5–7.6 | 7.0–7.6 |
| TOTAL | 100% | |

Those skilled in the art will recognize that changes may be made in form and detail of the invention described above, without departing from the spirit and scope of the invention. In addition, the invention is not to be taken as limited to all of the details thereof as modifications and variations thereof may be made without departing from the spirit or scope of the invention.

What is claimed is:

1. An emollient cream composition for application to the skin consisting of:
   between about 1.0 and 10.0 w/w percent sulfur;
   between about 5.0 and 15.0 w/w percent anhydrous sodium sulfacetamide;
   between about 0.1 and 1.0 w/w percent allantoin;
   water; xanthan gum; disodium EDTA; sodium thiosulfate; methyl paraben; propylene glycol; stearic acid; PEG-8 stearate; emulsifying wax; isopropyl myristate; propylene glycol stearate; propyl paraben; fragrance; and
   an effective amount of sodium hydroxide to maintain a pH at or above 7.0.

2. The composition of claim 1, wherein the amount of anhydrous sodium sulfacetamide is about 10.0 w/w percent.

3. The composition of claim 1, wherein the amount of sulfur is about 5.0 w/w percent.

4. The composition of claim 1, wherein the amount of allantoin is about 0.5 w/w percent.

5. The composition of claim 1, wherein sodium hydroxide is in the form of a 10 w/w percent solution and is present in the amount effective to maintain the pH of the composition at between about 7.5 and 7.6.

6. The composition of claim 1, wherein sodium hydroxide is in the form of a 10 w/w percent solution and is present in the amount of between about 1.0 to 4.0 w/w percent to maintain the pH of the composition at or above 7.0.

7. The composition of claim 1 wherein the composition has a pH of between about 7.5 and 7.6.

8. An emollient cream composition consisting of a mixture of:
- a gum phase of water, sodium sulfacetamide, sulfur, xanthan gum and allantoin;
- a water phase of water, disodium EDTA, sodium thiosulfate, methyl paraben and propylene glycol;
- an oil phase of stearic acid, PEG-8 stearate, emulsifying wax, isopropyl myristate, propylene glycol stearate and propyl paraben; and
- an effective amount of sodium hydroxide to maintain a pH at or above 7.0.

9. An emollient cream composition consisting of a mixture of:
- a gum phase consisting of between about 1.0 and 10.0 w/w percent sulfur, between about 5.0 and 15.0 w/w percent anhydrous sodium sulfacetamide, between about 0.1 and 1.0 w/w percent allantoin, water and a suspending agent;
- a water phase consisting of water, glycols, preservatives, solvents or combinations thereof;
- an oil phase consisting of fatty acids, waxes, glycols, surfactants or combinations thereof;
- optional fragrance; and
- an effective amount of sodium hydroxide to maintain a pH at or above 7.0.

* * * * *